(12) United States Patent
Cunningham et al.

(10) Patent No.: US 10,544,152 B2
(45) Date of Patent: Jan. 28, 2020

(54) 5-HT$_{2C}$R AGONIST ANALOGS

(71) Applicants: Kathryn A. Cunningham, Galveston, TX (US); Scott R. Gilbertson, Houston, TX (US)

(72) Inventors: Kathryn A. Cunningham, Galveston, TX (US); Scott R. Gilbertson, Houston, TX (US)

(73) Assignees: The Board of Regents of The University of Texas System, Austin, TX (US); University of Houston System, Houston, TX (US)

( * ) Notice: Subject to any disclaimer, the term of this patent is extended or adjusted under 35 U.S.C. 154(b) by 0 days.

(21) Appl. No.: 16/048,216

(22) Filed: Jul. 27, 2018

(65) Prior Publication Data
US 2019/0031672 A1    Jan. 31, 2019

Related U.S. Application Data

(60) Provisional application No. 62/538,344, filed on Jul. 28, 2017.

(51) Int. Cl.
| | | |
|---|---|---|
| *C07D 243/10* | (2006.01) | |
| *C07D 243/14* | (2006.01) | |
| *C07D 487/22* | (2006.01) | |

(52) U.S. Cl.
CPC ................ *C07D 487/22* (2013.01)

(58) Field of Classification Search
CPC ................ C07D 243/10; C07D 243/14
See application file for complete search history.

(56) References Cited

PUBLICATIONS

Soto, Claudia A., et al., Novel Bivalent 5-HT2A Receptor Antagonists Exhibit High Affinity and Potency in Vitro and Efficacy in Vivo, ACS Chem. Neurosci. Sep. 2018, 514-521 (2017).

*Primary Examiner* — Bruck Kifle
(74) *Attorney, Agent, or Firm* — Hylton-Rodic Law PLLC

(57) ABSTRACT

The invention relates to the novel analogs of selective 5HT$_{2C}$R agonist WAY163909, the preparation, and the use thereof.

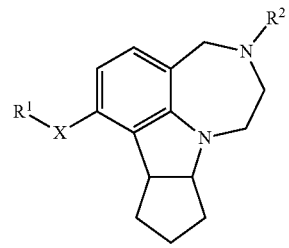

8 Claims, 5 Drawing Sheets

1 WAY163909

5-HT$_{2C}$R AGONIST ANALOGS

CROSS-REFERENCE TO RELATED APPLICATIONS

This application claims the benefit of U.S. Provisional Appl. No. 62/538,344, filed Jul. 28, 2017. The content of the aforesaid application is relied upon and is incorporated by reference herein in its entirety.

STATEMENT OF FEDERALLY SPONSORED RESEARCH AND DEVELOPMENT

This invention was made with government support under NIH/NIDA Grants Nos. P20 DA 024157 and P50 DA 033935 awarded by the National Institutes of Health (NIH) and National Institute on Drug Abuse (NIDA). The government has certain rights in the invention.

FIELD OF THE INVENTION

The field of the invention relates to novel analogs of selective 5HT$_{2C}$R agonist WAY163909, their preparation, and use thereof.

BACKGROUND

This background information is provided for the purpose of making information believed by the applicant to be of possible relevance to the present invention. No admission is necessarily intended, nor should it be construed, that any of the information disclosed herein constitutes prior art against the present invention.

Serotonin (5-hydroxytryptamine, 5-HT) receptors are implicated in a wide variety of physiological functions in both the central and peripheral nervous systems.

5-HT$_{2C}$ receptors have been implicated in a wide variety of diseases/conditions including obesity, anxiety, depression, obsessive compulsive disorder, schizophrenia, migraine and erectile dysfunction. See e.g., Dunlop, J., et al., CNS Drug Reviews 12:167-177 (2006). Consequently, this subtype of receptors is a valuable target for drug discovery. (7bR,10aR)-1,2,3,4,8,9,10,10a-octahydro-7bH-cyclopenta-[b][1,4]diazepino[6,7,1hi]indole} (commonly known as WAY-163909) a novel 5-HT2C receptor selective agonist has receive considerable attention. See e.g., Dunlop, J., et al., CNS Drug Reviews 12:167-177 (2006). WAY-163909 has been found to play a role in obesity, psychotic-like behavior and depression. See e.g., Dunlop, J., et al., CNS Drug Reviews 12:167-177 (2006). Accordingly, in addition to developing future therapeutics, there exists a need to develop to tools to study two 5-HT receptor (5-HT$_X$R$_S$) systems, the 5-HT$_{2A}$R and 5-HT$_{2C}$R. The 5-HT$_{2A}$R and 5-HT$_{2C}$R receptors are in oppositional control with 5-HT$_{2A}$R antagonists and 5-HT$_{2C}$R agonists exerting similar effects and acting in synergy on behaviors such as impulse control and reactivity to cocaine-associated cues. See e.g., Cunningham, K. A, et al., ACS Chem. Neurosci. 4:110-121 (2013).

Like many G-protein coupled receptors (GPCRs), these receptors are thought to exist and/or function as both homo- and/or heteromeric dimers. See e.g., Manica, F., et al., EMBO Reports 9(4), 363-369 (2008). The differing roles of these types of dimers is not fully understood, and the development of molecules that can serve as tools to biochemically and/or pharmacologically distinguish between the types of dimers is needed.

Furthermore, there exists a need for the development of probe molecules that can be used to investigate receptor location and relationship with other GPCRs. Moreover, there is a need to develop ligands that can be linked to other molecules including a second ligand, a reporter molecule (e.g., fluorescent dyes) or immobilization agents (e.g. biotin). A further challenge is to identify locations on known 5-HT$_X$R ligands that will allow for linking such groups without altering the ligands' binding and/or activity and successfully synthesize such compounds.

SUMMARY

Figure 1:
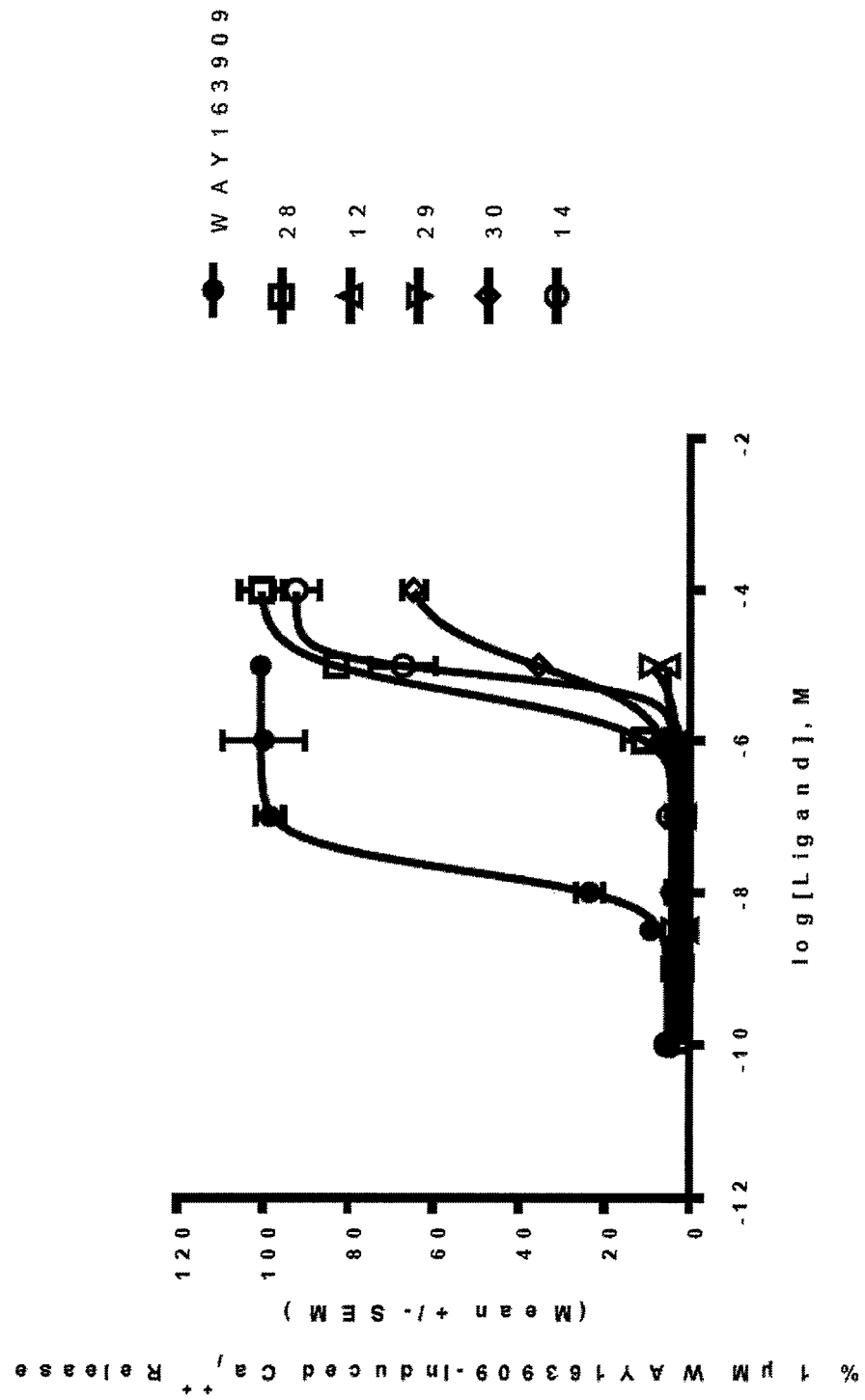
FIG. 1. Representative intracellular calcium release response of WAY163909 derivatives 28, 12, 29, 30, and 14 at human 5-HT2CR compared with WAY163909. The E$_{max}$ and EC$_{50}$ of these compounds are listed in Table 1.
Figure 2:
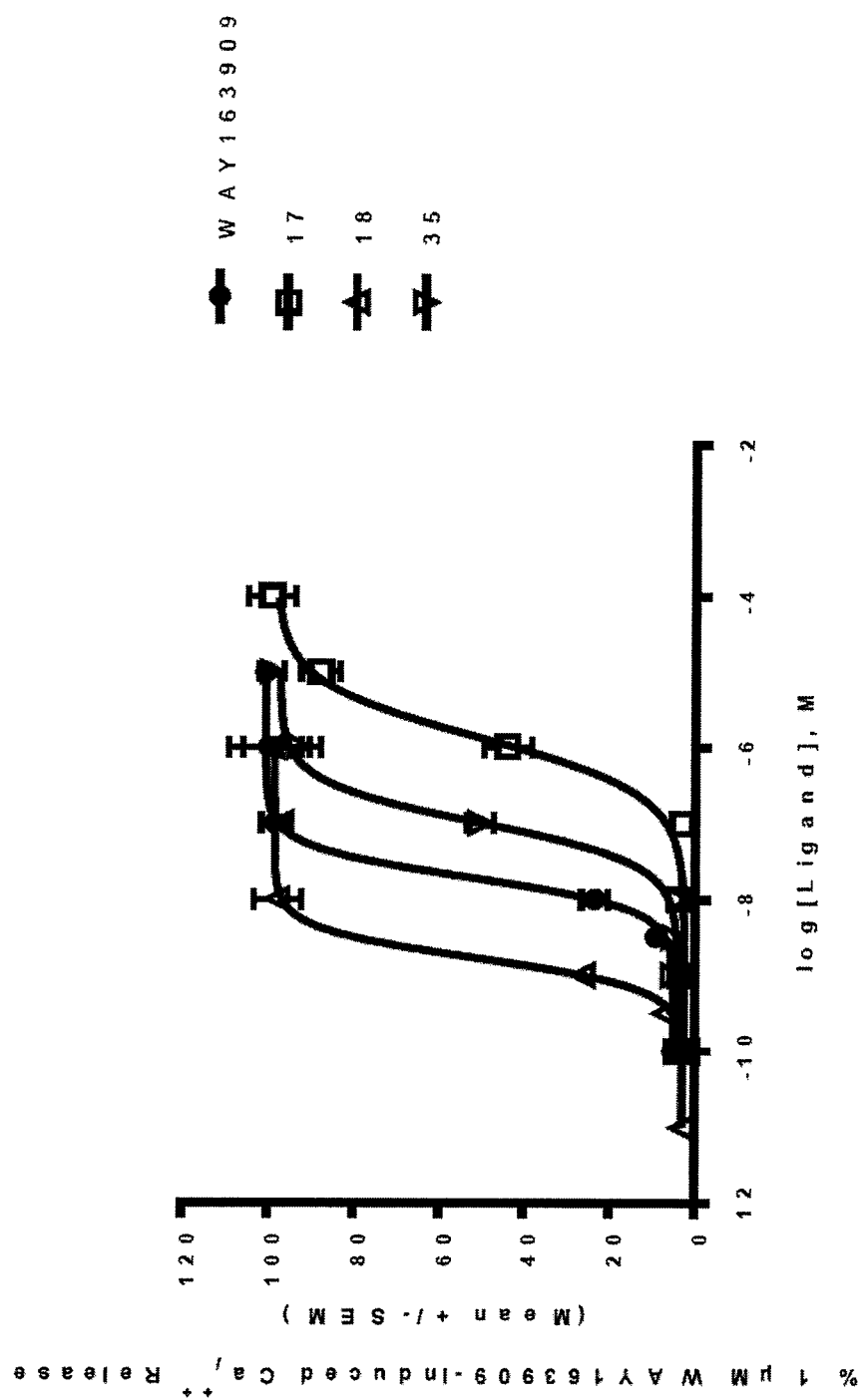
FIG. 2. Representative intracellular calcium release response of WAY163909 derivatives 17, 18, and 35 at human 5-HT2CR compared with WAY163909. The E$_{max}$ and EC$_{50}$ of these compounds are listed in Table 1.
Figure 3:
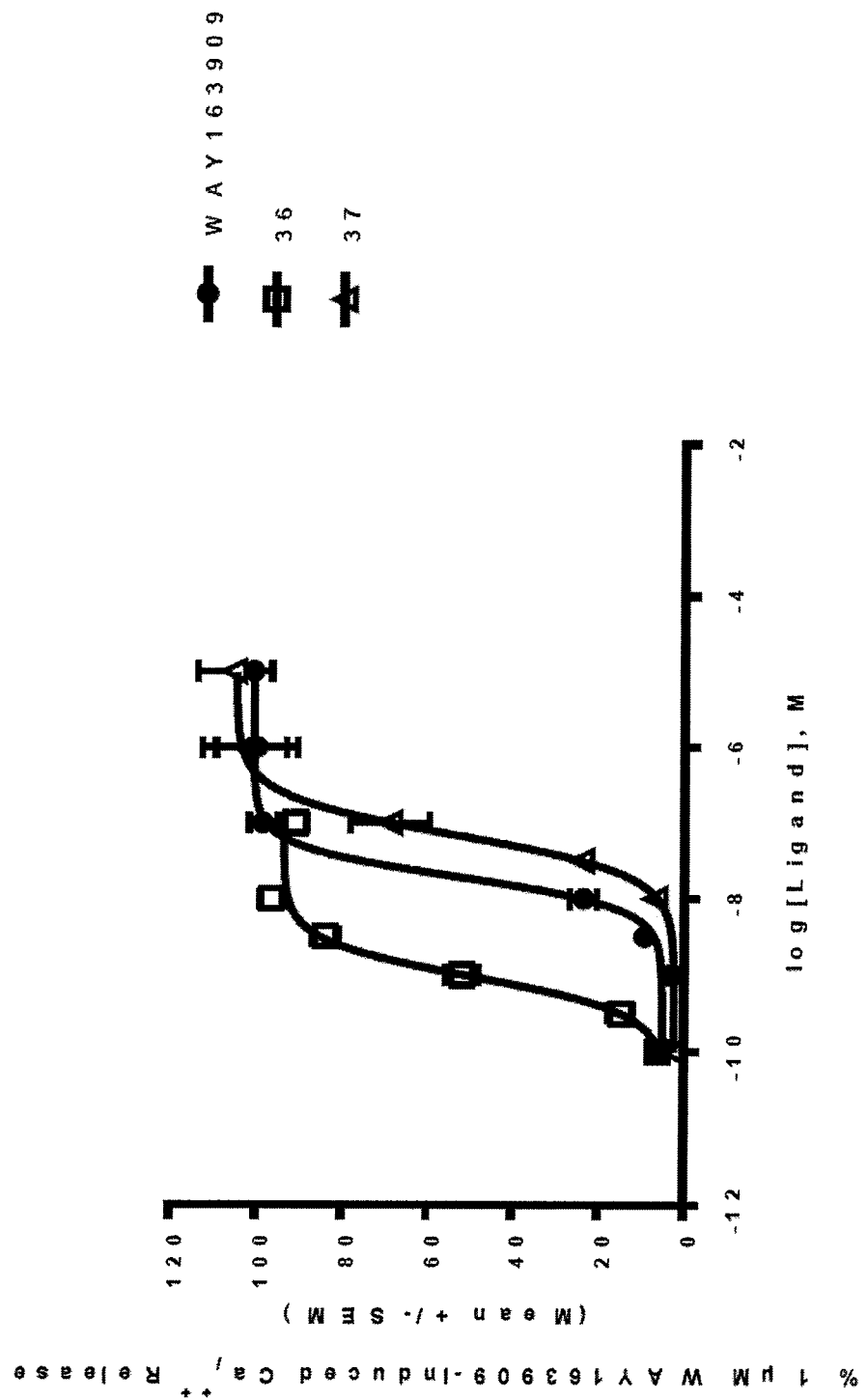
FIG. 3. Representative intracellular calcium release response of WAY163909 derivatives 36 and 37 at human 5-HT2CR compared with WAY163909. The E$_{max}$ and EC$_{50}$ of these compounds are listed in Table 1.
Figure 4:
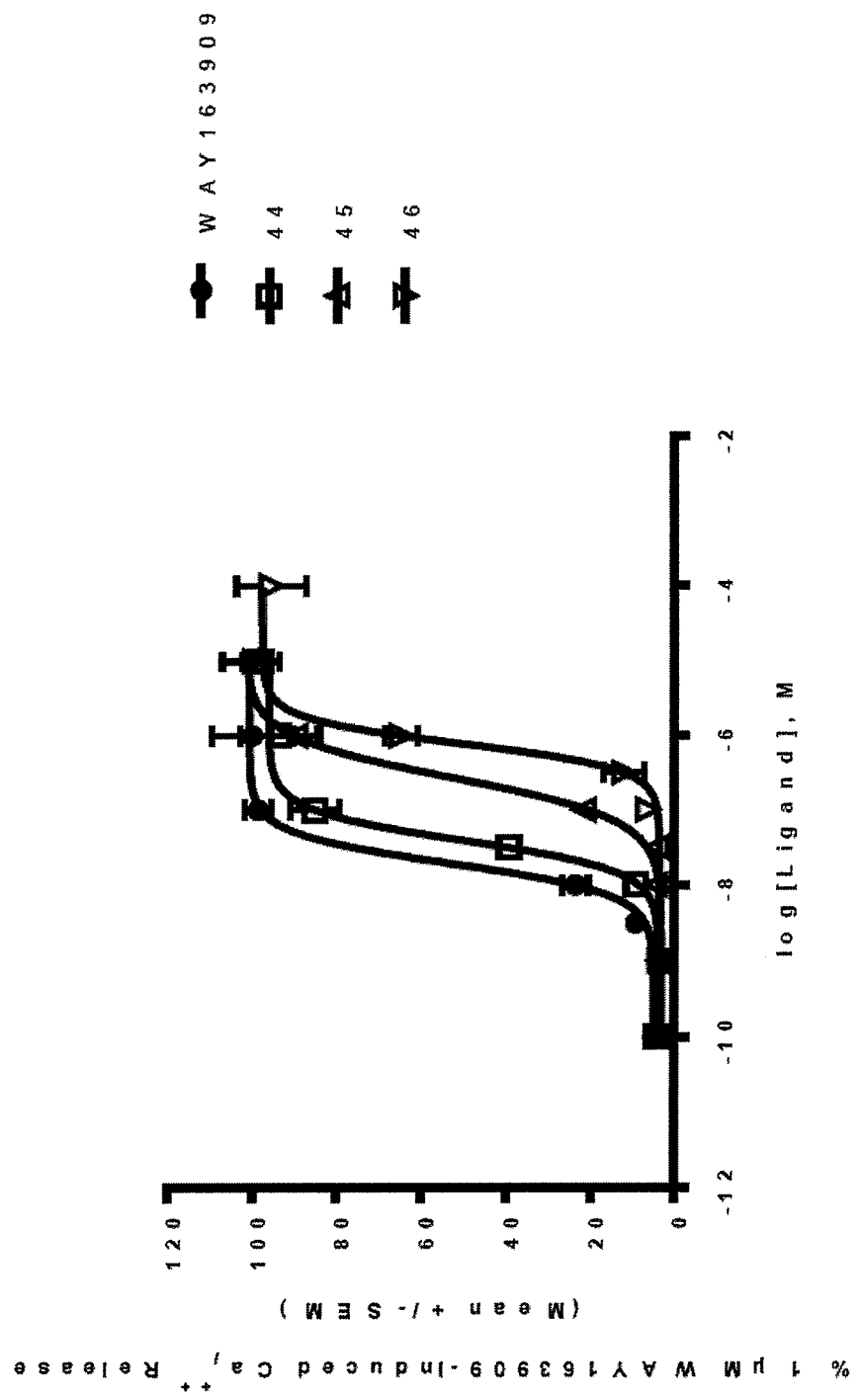
FIG. 4. Representative intracellular calcium release response of WAY163909 derivatives 44, 45, and 46 at human 5-HT2CR compared with WAY163909. The E$_{max}$ and EC$_{50}$ of these compounds are listed in Table 1.
Figure 5:
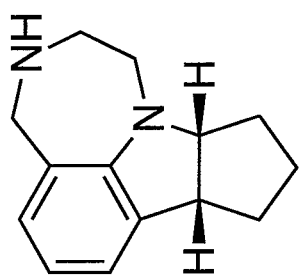
FIG. 5. WAY163909 chemical structure, compound 1.

The inventors have surprisingly discovered certain novel 5-HT2CR agonist analogs and have developed methods for preparing the same. The inventors have also discovered intermediate molecules for preparing these novel 5-HT2CR agonist analogs. One aspect of the invention pertains to compounds of Formula I, wherein:

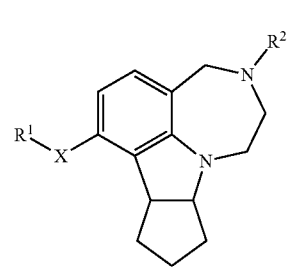

Formula I

R$^1$ is selected from the group consisting of alkyl, a polyether tether, a fluorophore, and an affinity probe;

R$^2$ is a N-protecting group or hydrogen; and wherein X is O or S.

In some embodiments, the invention encompasses a compound of Formula II, wherein R$^1$ is alkyl, a polyether tether, a fluorophore, or an affinity probe:

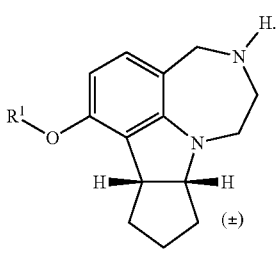

Formula II

In some embodiments, the invention encompasses a compound of Formula III, wherein $R^1$ is alkyl, a polyether tether, a fluorophore, or an affinity probe; $R^2$ is a N-protecting group:

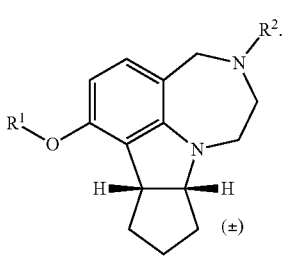

Formula III

In some embodiments, the invention encompasses a compound of Formula III, wherein, $R^1$ is alkyl, a polyether tether, a fluorophore, or an affinity probe; $R^2$ is a N-protecting group or hydrogen:

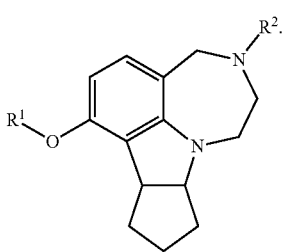

Formula Ia

Another aspect of the invention pertains to use of novel 5-HT2CR agonist analogs of the invention to induce $5\text{-}HT_{2C}R$-mediated intracellular calcium ($Ca^{2+}$) release.

Despcription

It is to be understood that both the foregoing general description of the invention and the following detailed description are exemplary, and thus do not restrict the scope of the invention.

All publications mentioned herein are incorporated by reference to the extent they support the present invention.

1.0. Definitions

For the purposes of promoting an understanding of the principles of the invention, reference will now be made to certain embodiments and specific language will be used to describe the same. It will nevertheless be understood that no limitation of the scope of the invention is thereby intended, and alterations and modifications in the illustrated invention, and further applications of the principles of the invention as illustrated therein are herein contemplated as would normally occur to one skilled in the art to which the invention relates.

Unless defined otherwise, all technical and scientific terms used herein have the same meaning as commonly understood by one of ordinary skill in the art to which this invention pertains.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

The use of "or" means "and/or" unless stated otherwise.

The use of "a" or "an" herein means "one or more" unless stated otherwise or where the use of "one or more" is clearly inappropriate.

The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" refers to a ±10% variation from the nominal value. It is to be understood that such a variation is always included in any given value provided herein, whether or not it is specifically referred to.

The term "pharmaceutically acceptable salt" refers to those salts of the compounds of the present invention which are, within the scope of sound medical judgment, suitable for use in contact with the tissues of patients without undue toxicity, and the like. As used herein, the term "pharmaceutically acceptable salt" may include acetate, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. (See S. M. Barge et al., "Pharmaceutical Salts," J. Pharm. Sci., 66:1-19 (1977)), which is incorporated herein by reference in its entirety, for further examples of pharmaceutically acceptable salt).

The term "fluorophore" refers to a fluorescent chemical compound that can re-emit light of a different wave length upon light excitation.

The term "affinity probe" refers to a molecule that can covalently be attached to an enzyme or receptor after binding to that enzyme or receptor in an reversible manner.

The term "polyether tether" refers to linker molecules that have possessing multiple ether groups.

The term "N-protecting group" refers to a nitrogen protecting group.

The term "TFA" refers to trifluoroacetic acid.

The term "rt" refers to room temperature.

The term "alkyl" as used herein by itself or as part of another group refers to both straight and branched chain radicals, and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The term "alkyl" may include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, and dodecyl.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, and N. The heteroatom(s) may be placed at any interior position of the heteroalkyl group or at the position at which the alkyl group is attached to the remainder of the molecule. Up to two heteroatoms may be consecutive.

The term "alkylene" as used herein refers to straight and branched chain alkyl linking groups, i.e., an alkyl group that links one group to another group in a molecule. In some embodiments, the term "alkylene" may include —$(CH_2)_n$— where n is 2-8.

The term "aryl" means a polyunsaturated hydrocarbon substituent. Aryl groups can be monocyclic or polycyclic (e.g., 2 to 3 rings that are fused together or linked covalently). Non-limiting examples of aryl and heteroaryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

The term "heteroaryl" as used herein refers to groups having 5 to 14 ring atoms; 6, 10 or 14 7π-electrons shared in a cyclic array; and containing carbon atoms and 1, 2 or 3 oxygen, nitrogen or sulfur heteroatoms. A heteroaryl group can be attached to the remainder of the molecule through a carbon or heteroatom. Especially preferred heteroaryl groups include 1,2,3-triazole, 1,2,4-triazole, 5-amino 1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, 2-aminopyridine, 4-aminopyridine, 2-aminoimidazoline, and 4-aminoimidazoline.

An "amino" group refers to an —$NH_2$ group.

A "carboxylic acid" group refers to a $CO_2H$ group.

An "alkynyl group" refers to a straight or branched chain radical of 2-20 carbon atoms, unless the chain length is limited thereto, wherein there is at least one triple bond between two of the carbon atoms in the chain, including, but not limited to, acetylene, 1-propylene, 2-propylene, and the like. In some embodiments, "alkynyl group" refers to an alkynyl chain, which is 2 to 10 carbon atoms in length. In other embodiments, "alkynyl group" refers to an alkynyl chain, which is more 2 to 8 carbon atoms in length. In further embodiments, "alkynyl group" refers to an alkynyl chain, which is from 2 to 4 carbon atoms in length.

An "amido" group refers to an —$CONH_2$ group. An alkylamido group refers to an —CONHR group wherein R is as defined above. A dialkylamido group refers to an —CONRR' group wherein R and R' are as defined above.

The term "halogen" or "halo" as used herein by itself or as part of another group refers to chlorine, bromine, fluorine or iodine.

The term "hydroxy" or "hydroxyl" as used herein by itself or as part of another group refers to an —OH group.

An "alkoxy" group refers to an —O-alkyl group wherein "alkyl" is as defined above. In one embodiment, the alkyl group has 1-12 carbons. In another embodiment, the alkyl group has 1-7 carbons. In a further embodiment, the alkyl group has 1-6 carbons. In another embodiment, the alkyl group has 1-4 carbons.

A "thio" group refers to an —SH group.

An "alkylthio" group refers to an —SR group wherein R is alkyl as defined above.

The term "heterocycle" or "heterocyclic ring", as used herein except where noted, represents a stable 5- to 7-membered monocyclic-, or stable 7- to 11-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Rings may contain one oxygen or sulfur, one to three nitrogen atoms, or one oxygen or sulfur combined with one or two nitrogen atoms. The heterocyclic ring may be attached at any heteroatom or carbon atom that results in the creation of a stable structure.

The term "alkylamino" as used herein by itself or as part of another group refers to an amino group which is substituted with one alkyl group having from 1 to 6 carbon atoms. The term "dialkylamino" as used herein by itself or as part of another group refers to an amino group which is substituted with two alkyl groups, each having from 1 to 6 carbon atoms.

The term "arylamine" or "arylamino" as used herein by itself or as part of another group refers to an amino group which is substituted with an aryl group, as defined above.

As used herein, the term "arylalkyl" denotes an alkyl group substituted with an aryl group, for example, Ph-$CH_2$— etc.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, alkyl, heteroalkyl, alkoxy, alkylthio, alkylamino, (alkyl)$_2$amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects, the optional substituents may be further substituted with one or more substituents independently selected from: halogen, nitro, cyano, hydroxy, amino, mercapto, formyl, carboxy, carbamoyl (—$C(O)NR_2$), unsubstituted alkyl, unsubstituted heteroalkyl, alkoxy, alkylthio, alkylamino, (alkyl)$_2$amino, alkyl sulfinyl, alkyl sulfonyl, aryl sulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, $C_{1-4}$alkyl, phenyl, benzyl, —$NH_2$, —NH($C_{1-4}$alkyl), —N(C1-4alkyl)$_2$, —$NO_2$, —S($C_{1-4}$alkyl), —$SO_2$($C_{1-4}$ alkyl), —$CO_2$($C_{1-4}$alkyl), and —O($C_{1-4}$alkyl).

2.0. Compounds

The inventors surprisingly discovered novel analogs of selective 5-$HT_{2C}R$ agonist WAY 163909, which may be used as tools to study two 5-HT receptors (5-HTXRs) systems, the 5-$HT_{2A}R$ and 5-$HT_{2C}R$. One obstacle that the inventors overcame in developing the invention is the difficulty in synthesizing these molecules. Another challenge that inventors overcame was derivatizing the WAY163909 scaffold while maintaining activity.

The inventors also surprisingly discovered ceratin novel analogs of selective 5-$HT_{2C}R$ agonist WAY 163909, with agonist activity.

One aspect of the invention pertains to compounds of Formula I, wherein:

Formula I

R¹ is selected from the group consisting of alkyl, a polyether tether, a fluorophore, and an affinity probe;
R² is a N-protecting group or hydrogen; and
wherein X is O or S.

In further embodiments, the invention encompasses compounds described herein wherein R¹ is a fluorophore selected from the group consisting of:
Alkyne cyanine dye 718,
Alkyne MegaStokes dye 608,
Alkyne MegaStokes dye 673,
Alkyne MegaStokes dye 735,
Azide cyanine dye 728,
Azide-fluor 488,
Azide-fluor 545,
Azide-PEG3-biotin conjugate,
Biotin-PEG4-alkyne,
Cy3-alkyne,
Cy3-azide,
Cy5-azide,
DBCO-Cy3,
DBCO-Cy5,
Dibenzocyclooctyne-fluor 488,
Fluor 488-Alkyne,
Fluor 545-Alkyne, and
NVOC2-Q-rhodamine-5-PEG3-azide.

In one aspect of the invention, Formula I is a racemate. In another aspect of the invention, Formula I is a (R,R)-, (R,S)-, (S,R)-, or (S,S) enantiomer, or a combination thereof.

In some embodiments, the invention encompasses compounds of Formula I wherein X is O; R² is hydrogen; and R¹ is a polyether tether of the following structure:

wherein R³ is an alkynyl, fluorophore, an affinity probe, or —CH₂—R⁴, wherein R⁴ is azido, —CO₂H, or —NH₂; and wherein n is 0-20.

In some embodiments, n is 0-5. In other embodiments, n is 0-8. In further embodiments, n is 1-4. In some embodiments, n is 1-8. In other embodiments, n is 1-5.

In further embodiments, the invention encompasses compounds of Formula I, wherein R² is a N-protecting group selected from the group consisting of CBz and —(CO)R⁵, wherein R⁵ is alkyl or aryl.

In further embodiments, the invention encompasses compounds of Formula II wherein R¹ is alkyl, a polyether tether, a fluorophore, or an affinity probe:

Formula II

In further embodiments, the invention encompasses a compound of Formula II, wherein R¹ is methyl.

In one aspect of the invention, Formula II is a racemate. In another aspect of the invention, Formula II is a (R,R)-, (R,S)-, (S,R)-, or (S,S) enantiomer, or a combination thereof.

In some embodiments, the compound of Formula II is:

Formula IIa

Formula IIb

In certain embodiments, the compound of Formula II is one of:

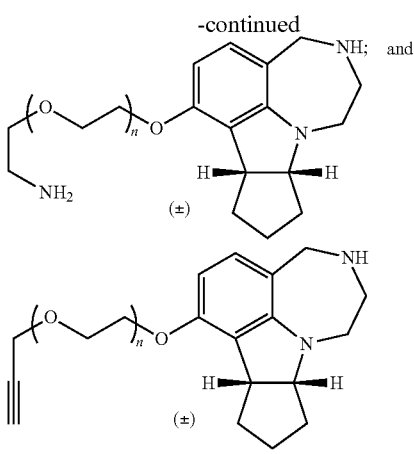

wherein n is 0-20. In some embodiments, n is 0-5. In other embodiments, n is 0-8. In further embodiments, n is 1-4. In some embodiments, n is 1-8. In other embodiments, n is 1-5.

One aspect of the invention pertains to compounds of Formula III wherein $R^1$ is alkyl, a polyether tether, a fluorophore, or an affinity probe; $R^2$ is a N-protecting group; and X is O:

Formula III

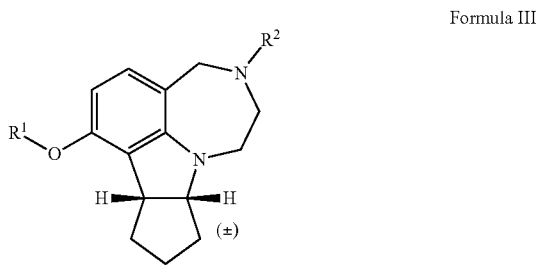

In one aspect of the invention, Formula III is a racemate. In another aspect of the invention, Formula III is a (R,R)-, (R,S)-, (S,R)-, or (S,S) enantiomer, or a combination thereof.

In further embodiments, the invention encompasses compounds of Formula III, wherein $R^2$ is a N-protecting group selected from the group consisting of CBz and —(CO)$R^5$, wherein $R^5$ is alkyl or aryl.

In some embodiments, the compound of Formula III is:

Formula IIIa

Formula IIIb

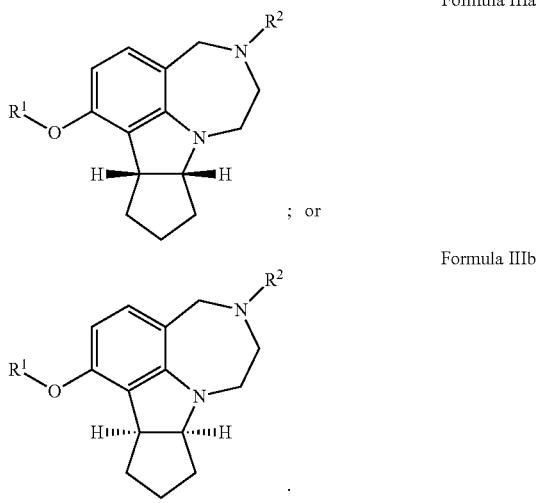

In some embodiments, the invention encompasses a compound of Formula Ia, wherein $R^1$ is alkyl, a polyether tether, a fluorophore, or an affinity probe; $R^2$ is a N-protecting group or hydrogen:

Formula Ia

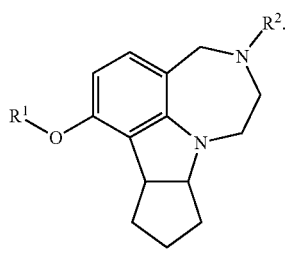

2.1 Synthesis of Compounds of the Invention

The description of preparation of certain compounds of the invention is meant to be exemplary of certain embodiments of the invention. The reagents and reactant used for synthetic conversions outlined herein and below is merely exemplary. The invention contemplates using the same or different reagents discussed herein to achieve preparation of the compounds of the invention.

Certain embodiments of the invention may be synthesized by linking a molecule to the A ring of the WAY163909 scaffold (see FIG. 1) as exemplified by preparation of compound 18 (Scheme 1):

Scheme 2. Synthetic Route for Certain Compounds of Formula I

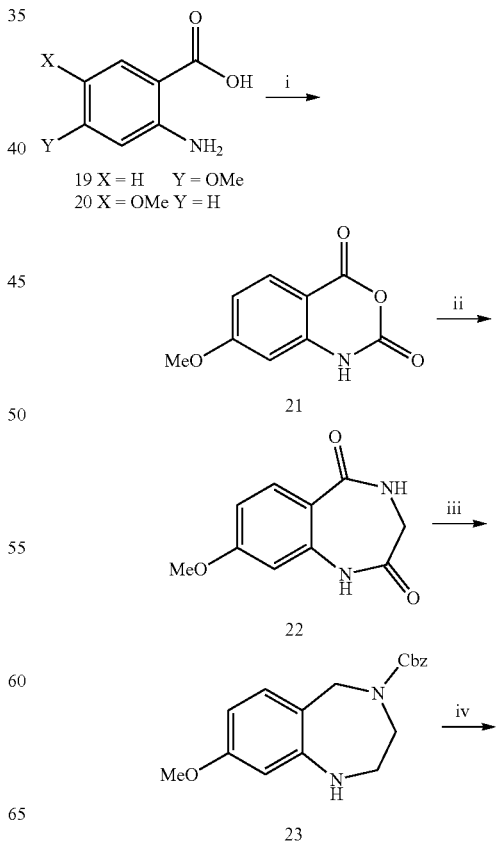

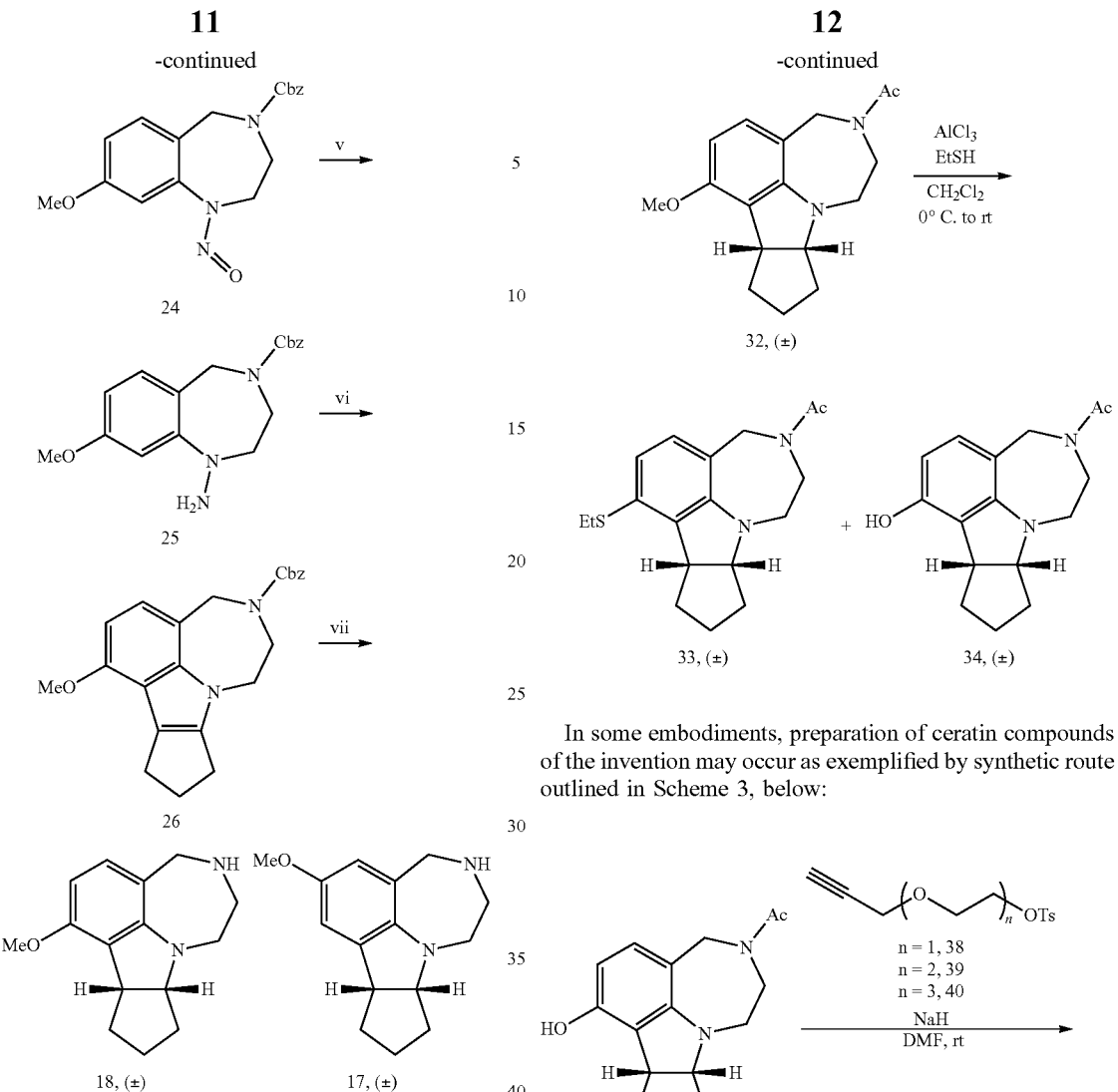

Reagents and conditions: (i) triphosgene, THF, rt, 18 h; (ii) glycine, 6N NaOH, H₂O, reflux, 12 h, then L-tartaric acid, reflux, 2 h, 77%; (iii) a. LAH, THF, reflux, 48 h; b. benzyl chloroformate, Et₃N, CH₂Cl₂, rt, 18 h, 77%; (iv) NaNO₂, 1N HCl, H₂O, 1,4-dioxane, rt, 15 min; (v) TiCl₄, Mg, CH₂Cl₂, diethyl ether, rt, 15 min; (vi) cyclopentanone, p-TSA, toluene, reflux, 3 h; (vii) a. NaBH₄, TFA, rt, 10 min; b. 10% Pd/C, H₂, THF, rt, 3 h. Steps for 17 are the same as 18.

In some embodiments, preparation of certain compounds of the invention may involve removal of a Cbz-protecting group as exemplified by preparation of compound 34 (Scheme 2), and may include further removal of the N-acetyl group:

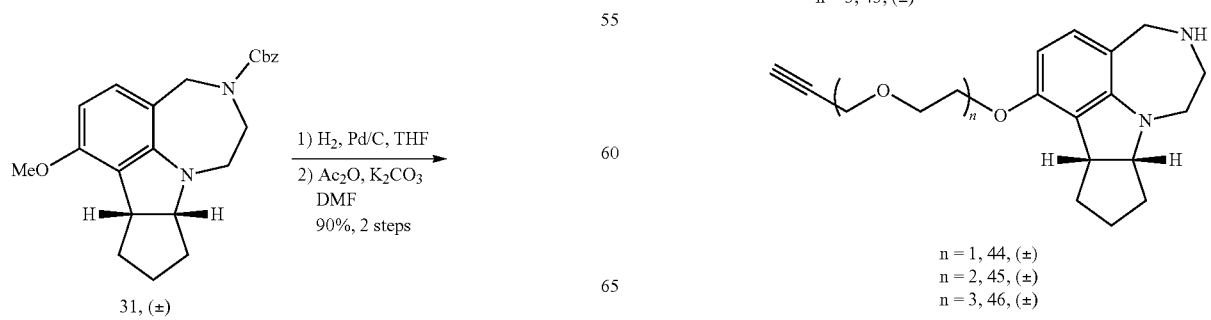

In some embodiments, preparation of ceratin compounds of the invention may occur as exemplified by synthetic route outlined in Scheme 3, below:

3.0 METHOD OF USE

Another aspect of the invention pertains generally to the use of compounds of invention to induce 5-$HT_{2C}$R-mediated intracellular calcium ($Ca^{2+}$) release. In some embodiments, the invention encompasses a method of inducing 5-$HT_{2C}$R-mediated intracellular calcium ($Ca^{2+}$) release by contacting a cell with one or more compounds of the invention and/or a pharmaceutical salt thereof.

In some embodiments, the invention encompasses a method of inducing 5-$HT_{2C}$R-mediated intracellular calcium ($Ca^{2+}$) release by contacting a cell with one or more compounds of Formula I or Ia, a pharmaceutical salt thereof, or a combination thereof.

In some embodiments, the invention encompasses a method of inducing 5-$HT_{2C}$R-mediated intracellular calcium ($Ca^{2+}$) release by contacting a cell with one or more compounds of Formula II, IIa, or IIb, a pharmaceutical salt thereof, or a combination thereof.

In some embodiments, the invention encompasses a method of inducing 5-$HT_{2C}$R-mediated intracellular calcium ($Ca^{2+}$) release by contacting a cell with one or more compounds of Formula III, IIIa, IIIb, a pharmaceutical salt thereof, or a combination thereof.

4.0 EXAMPLES

The following examples are provided solely to illustrate the present invention and are not intended to limit the scope of the invention, described herein.

Example 1

Cell Lines and Cell Culture.

The PathHunter® U2OS HTR2C β-Arrestin cell line (5-$HT_{2C}$R-U2OS; DiscoveRx) stably express the nonedited human 5-$HT_{2C}$R isoform (h5-$HT_{2C}$R). The 5-$HT_{2C}$R-U2OS cells were grown in Assay Complete™ U2OS Medium 31 (DiscoveRx) at 37° C., 5% $CO_2$ and 85% relative humidity according to manufacturer's recommendations utilizing AssayComplete™ Cell Detachment Reagent (DiscoveRx). Cells were passaged at 70-80% confluence and all experiments were conducted using cells in log phase growth.

Intracellular Calcium Assay.

The ability of the molecules to act as agonists to induce 5-$HT_{2C}$R-mediated intracellular calcium ($Ca_i^{++}$) release was conducted in an U2OS cell line stably expressing the human 5-$HT_{2C}$R. For all molecules examined, the observed potency was shifted rightward relative to 5-HT or WAY163909 (Table 1).

Intracellular calcium ($Ca_i^{++}$) release was monitored using the FLIPR Calcium 4 Assay Kit (Molecular Devices) according to previously published protocols with minor modifications. See, e.g., Shashack, M. J., et al., ACS Chem Neurosci. 2 (11), 640-644 (2011); Seitz, P. K.; Bremer, N. M., et al., BMC Neurosci. 13, 25 (2012).

Cells were plated at 5,000-7,000 cells/well in Assay Complete™ Cell Plating Reagent 16 (DiscoveRx) in black-sided, clear bottomed 96-well tissue culture plates and allowed to adhere overnight. Medium was removed and replaced with 40 µl Hank's balanced salt solution without calcium, magnesium and phenol red (HBSS; Corning) plus 40 µl Calcium 4 dye solution in Buffer B supplemented with 2.5 mM probenecid (Sigma-Aldrich) to inhibit extracellular dye transport. Plates were incubated for 60 min at 37° C. followed by 30 min at room temperature in the dark.

Fluorescence ($\lambda_{ex}$=485 nm, $\lambda_{em}$=525 nm) was measured using a FlexStation3 (Molecular Devices). Baseline was established for 17 secs before addition of 20 µl vehicle (HBSS without calcium or magnesium) or 5× concentrated compound. Addition of 5-HT, WAY163909, or ligand occurred at the 17-sec time point and fluorescence was recorded every 1.7 sec for 120 sec. Maximum peak height was determined using FlexStation software (SoftMax Pro 5.4). After the final readings, cells were fixed in 2% paraformaldehyde overnight.

Data Analysis

Peak responses from each well were normalized to total cell mass as determined with crystal violet staining. See e.g., Ding, C. et al., ACS Chem. Neurosci 3 (7), 538-545 (2012). The $E_{max}$ is defined as the maximum possible $Ca_i^{++}$ response and data are expressed as a percent of the $Ca_i^{++}$ release obtained with 1 µM of WAY163909. Potency of the compounds was determined using the $EC_{50}$ (concentration of compound required to achieve half-maximal response). The $EC_{50}$ values were determined using 4-parameter nonlinear regression analysis and calculated from at least three independent experiments, each conducted in triplicate, and are presented as mean±SEM. Ratkowsky, D. A., et al., Biometrics 42, 575-582 (1986). An $EC_{50}$ or $E_{max}$ value was not calculated for ligands that failed to reach a plateau.

TABLE 1

Activity of ceratin exemplary embodiments of the invention in U2OS cell line stably expressing the 5-HT2CR.

| Cpd # | Structure | $^aEC_{50}$ nM ± SEM | $^bE_{max}$ |
|---|---|---|---|
| 27 | 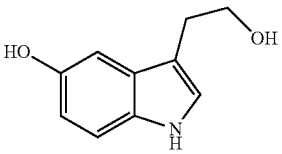 [SMILES: OCCc1c[nH]c2ccc(O)cc12] | 0.33 ± 0.1 | 100 |

TABLE 1-continued

Activity of ceratin exemplary embodiments of the invention in U2OS cell line stably expressing the 5-HT2CR.

| Cpd # | Structure | $^{a}EC_{50}$ nM ± SEM | $^{b}E_{max}$ |
|---|---|---|---|
| 1 (±) | 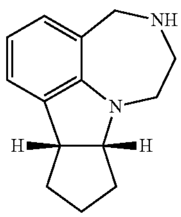 [SMILES: c1cc2c3c(c1)[C@H]1CCC[C@H]1N3CCNC2] | 18.2 ± 2.6 | 100 |
| 28 (±) | 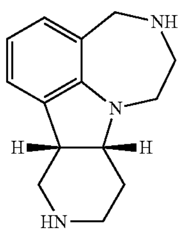 [SMILES: c1cc2c3c(c1)[C@H]1CNCC[C@H]1N3CCNC2] | $^{c}NC$ | $^{c}NC$ |
| 12 (±) | 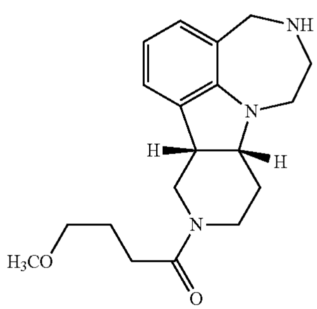 [SMILES: COCCCC(=O)N1CC[C@@H]2[C@H](C1)c1cccc3c1N2CCNC3] | $^{c}NC$ | $^{c}NC$ |
| 29 (±) | 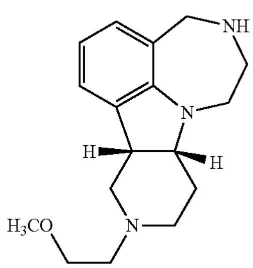 [SMILES: COCCN1CC[C@@H]2[C@H](C1)c1cccc3c1N2CCNC3] | $^{c}NC$ | $^{c}NC$ |
| 30 (±) | 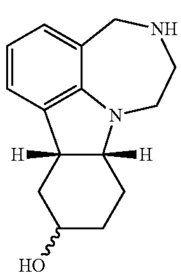 [SMILES: OC1CC[C@@H]2[C@H](C1)c1cccc3c1N2CCNC3] | $^{c}NC$ | $^{c}NC$ |
| 18 (±) | 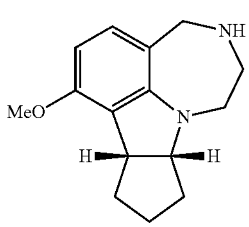 [SMILES: COc1ccc2c3c1[C@H]1CCC[C@H]1N3CCNC2] | 2.4 ± 0.4 | 102.9 ± 4.6 |

TABLE 1-continued

Activity of ceratin exemplary embodiments of the invention in U2OS cell line stably expressing the 5-HT2CR.

| Cpd # | Structure | $EC_{50}$ nM ± SEM [a] | $E_{max}$ [b] |
|---|---|---|---|
| 35 (±) | 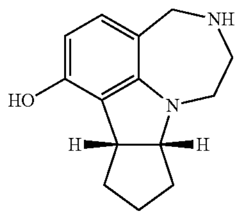 [SMILES: Oc1ccc2c3c1[C@H]1CCC[C@H]1N3CCNC2] | 119.4 ± 11.5 | 95.9 ± 2.6 |
| 44 (±) | 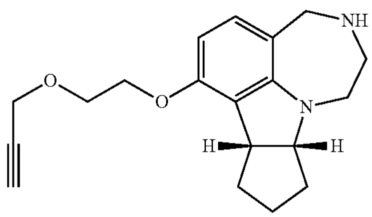 [SMILES: C#CCOCCOc1ccc2c3c1[C@H]1CCC[C@H]1N3CCNC2] | 51.9 ± 9.6 | 97.2 ± 2.3 |
| 45 (±) | 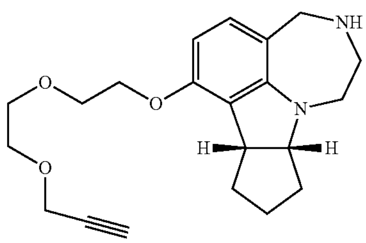 [SMILES: C#CCOCCOCCOc1ccc2c3c1[C@H]1CCC[C@H]1N3CCNC2] | 218.0 ± 53.1 | 99.3 ± 2.2 |
| 46 (±) | 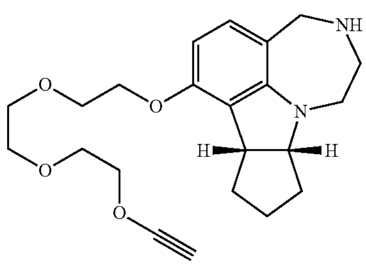 [SMILES: C#COCCOCCOCCOc1ccc2c3c1[C@H]1CCC[C@H]1N3CCNC2] | 574.9 ± 112.0 | 95.2 ± 2.3 |
| 36 (±) | 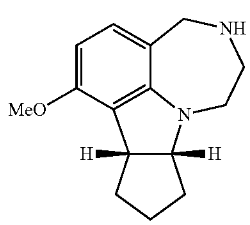 [SMILES: COc1ccc2c3c1[C@H]1CCC[C@H]1N3CCNC2] | 1.2 ± 0.3 | 105.1 ± 6.1 |
| 14 (±) | 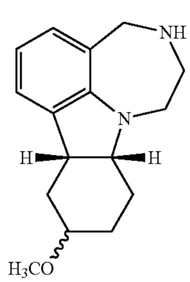 | NC [c] | NC [c] |

TABLE 1-continued

Activity of ceratin exemplary embodiments of the invention in U2OS cell line stably expressing the 5-HT2CR.

| Cpd # | Structure | $^aEC_{50}$ nM ± SEM | $^bE_{max}$ |
|---|---|---|---|
| 17 (±) | MeO, structure with NH, H, H | 1484 ± 237.7 | 95.9 ± 1.5 |
| 37 | structure with NH, MeO, H, H | 72.4 ± 14.5 | 97.6 ± 4.7 |

$^a$mean ± SEM
$^b$% Ca$_i^{++}$ release obtained with 1 μM of WAY163909 (1);
$^c$NC = not calculated

Example 2

Preparation of Exemplary Embodiments of the Invention

The characterization data for certain exemplary compounds of the invention is presented below.

2.1. Synthesis of 7-methoxy-2,3,4,7b,8,9,10,10a-octahydro-1H-cyclopenta[b][1,4]diazepino[6,7,1-hi]indole (compound 18, racemate of 36/37)

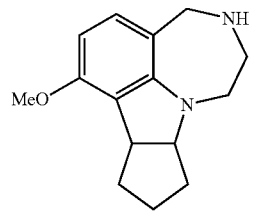 [SMILES: COc1ccc2c3c1C1CCCC1N3CCNC2]

To a solution of benzyl 7-methoxy-4,7b,8,9,10,10a-hexahydro-1H-cyclopenta[b][1,4]diazepino[6,7,1-hi]indole-3(2H)-carboxylate (94 mg, 0.25 mmol) in methanol (5.5 mL) was added 40 mg of 10% Pd/C. The mixture was stirred under hydrogen gas atmosphere for 3 hours. The suspension was filtered through a firm pad of celite and wash with 20% methanol in dichloromethane until no more UV active species came out. Evaporation of the solvent afforded the crude product as a yellowish oil (60.5 mg, 0.24 mmol, 99%).
$^1$H NMR (500 MHz, CDCl$_3$) δ 6.80 (d, J=8.1 Hz, 1H), 6.22 (d, J=8.1 Hz, 1H), 3.98-3.90 (m, 2H), 3.84-3.76 (m, 4H), 3.68 (d, J=15.2 Hz, 1H), 3.28-3.22 (m, 1H), 3.19-3.15 (m, 1H), 2.85 (p, J=11.3 Hz, 2H), 1.95-1.80 (m, 2H), 1.76-1.53 (m, 4H). $^{13}$C NMR (126 MHz, CDCl$_3$) δ 154.7, 153.9, 127.7, 121.5, 119.4, 101.0, 73.4, 56.9, 55.1, 54.3, 51.2, 43.7, 34.2, 33.4, 24.6. FIRMS (ESI-TOF) Calcd. for C$_{15}$H$_{20}$N$_2$O [M+H]$^+$: 245.1648; found: 245.1650.

2.2. Synthesis of 7-(2-(Prop-2-ynyloxy)ethoxy)-2,3,4,7b,8,9,10,10a-octahydro-1H-cyclopenta[b][1,4]diazepino[6,7,1-hi]indole (compound 44)

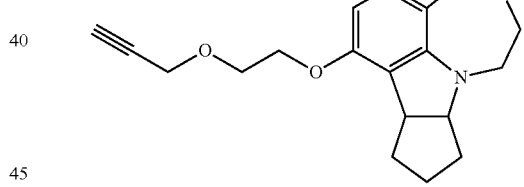

1-(7-(2-(Prop-2-ynyloxy)ethoxy)-8,9,10,10a-tetrahydro-1H-cyclopenta[b][1,4]diazepino[6,7,1-hi]indol-3(2H,4H,7bH)-yl)ethanone (107 mg, 0.3 mmol) was dissolved in mixture of methanol (7.5 mL) and 2 N HCl (7.5 mL). The mixture was heated to reflux for 48 hours. The solvent was evaporated and the residue was suspended in 20% methanol in dichloromethane. The suspension was filtered and washed with 20% methanol in dichloromethane until no UV active species appearing. Evaporation of the solvent yielded the crude residue, which was purified by column chromatography (20% methanol in dichloromethane) to generate the desired product as a yellowish oil (92 mg, 0.29 mmol, 98%).
$^1$H NMR (500 MHz, CDCl$_3$) δ 6.76 (d, J=8.2 Hz, 1H), 6.19 (d, J=8.4 Hz, 1H), 4.27 (d, J=2.3 Hz, 2H), 4.19-4.08 (m, 2H), 3.95 (d, J=15.3 Hz, 1H), 3.93-3.86 (m, 3H), 3.82 (td, J=9.1, 3.2 Hz, 1H), 3.68 (d, J=15.2 Hz, 1H), 3.28 (dd, J=12.0, 3.8 Hz, 1H), 3.17 (dd, J=10.7, 3.9 Hz, 1H), 2.91-2.80 (m, 2H), 2.57 (br, 1H), 2.45 (t, J=2.3 Hz, 1H), 1.94-1.80 (m, 2H), 1.78-1.51 (m, 4H). $^{13}$C NMR (126 MHz, CDCl$_3$) δ 169.6, 168.8, 154.4, 154.0, 153.3, 153.0, 128.6, 127.3, 122.5, 121.9, 115.5, 114.3, 102.7, 102.1, 79.5, 79.5, 74.5, 74.5, 73.3, 73.3, 68.1, 67.3, 58.4, 58.4, 53.5, 52.2, 51.3, 48.9, 47.8, 43.5, 43.5, 34.3, 34.2, 33.3, 33.2, 24.5, 22.0, 21.7. HRMS (ESI-TOF) Calcd. for $C_{19}H_{24}N_2O_2$ [M+H]$^+$: 313.1911; found: 313.1914.

2.3. Synthesis of 7-(2-(2-(prop-2-ynyloxy)ethoxy)ethoxy)-2,3,4,7b,8,9,10,10a-octahydro-1H-cyclopenta[b][1,4]diazepino[6,7,1-hi]indole (45)

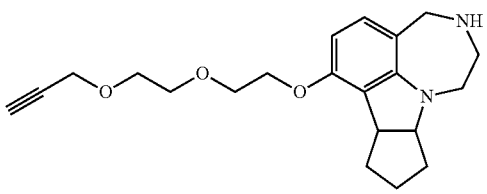 [SMILES: C#CCOCCOCCOc1ccc2c3c1C1CCCC1N3CCNC2]

1-(7-(2-(2-(Prop-2-ynyloxy)ethoxy)ethoxy)-8,9,10,10a-tetrahydro-1H-cyclopenta[b][1,4]diazepino[6,7,1-hi]indol-3(2H,4H,7bH)-yl)ethanone (234.4 mg, 0.59 mmol) was dissolved in mixture of methanol (10 mL) and 2 N HCl (10 mL). The mixture was heated to reflux for 48 hours. The solvent was evaporated and the residue was suspended in 20% methanol in dichloromethane. The suspension was filtered and washed with 20% methanol in dichloromethane until no UV active species appearing. Evaporation of the solvent yielded the crude residue, which was purified by column chromatography (10% methanol in dichloromethane) to generate the desired product as a yellowish solid (157.7 mg, 0.44 mmol, 75%).

$^1$H NMR (500 MHz, CDCl$_3$) δ 6.80 (d, J=8.3 Hz, 1H), 6.22 (d, J=8.2 Hz, 1H), 4.96 (br, NH), 4.21 (d, J=2.3 Hz, 2H), 4.16-4.09 (m, 2H), 4.04 (d, J=15.1 Hz, 1H), 3.92 (dd, J=8.8, 5.1 Hz, 1H), 3.84 (t, J=4.9 Hz, 2H), 3.81 (dd, J=8.8, 3.2 Hz, 1H), 3.77-3.74 (m, 2H), 3.74-3.69 (m, 3H), 3.39 (dd, J=13.2, 3.1 Hz, 1H), 3.20 (dd, J=12.6, 2.5 Hz, 1H), 3.03-2.88 (m, 2H), 2.43 (t, J=2.3 Hz, 1H), 1.93-1.80 (m, 2H), 1.77-1.60 (m, 3H), 1.60-1.49 (m, 1H). $^{13}$C NMR (126 MHz, CDCl$_3$) δ 154.3, 153.9, 128.4, 122.1, 115.7, 102.6, 79.6, 74.5, 73.5, 70.6, 69.8, 69.1, 67.5, 58.4, 54.5, 52.7, 50.0, 43.8, 34.4, 33.3, 24.5. HRMS (ESI-TOF) Calcd. for $C_{21}H_{28}N_2O_3$ [M+H]$^+$: 357.2173; found: 357.2178.

2.4. Synthesis of 7-(2-(2-(2-(prop-2-ynyloxy)ethoxy)ethoxy)ethoxy)-2,3,4,7b,8,9,10,10a-octahydro-1H-cyclopenta[b][1,4]diazepino[6,7,1-hi]indole (46)

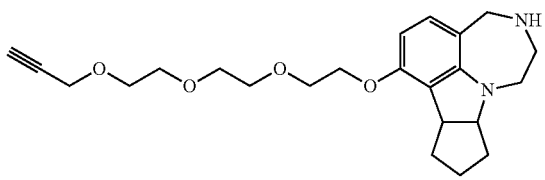 [SMILES: C#CCOCCOCCOCCOc1ccc2c3c1C1CCCC1N3CCNC2]

1-(7-(2-(2-(2-(Prop-2-ynyloxy)ethoxy)ethoxy)ethoxy)-8,9,10,10a-tetrahydro-1H-cyclopenta[b][1,4]diazepino[6,7,1-hi]indol-3(2H,4H,7bH)-yl)ethanone (154 mg, 0.35 mmol) was dissolved in mixture of methanol (11.5 mL) and 2 N HCl (11.5 mL). The mixture was heated to reflux for 48 hours. The solvent was evaporated and the residue was suspended in 20% methanol in dichloromethane. The suspension was filtered and washed with 20% methanol in dichloromethane until no UV active species appearing. Evaporation of the solvent yielded the crude residue, which was purified by column chromatography (10% methanol in dichloromethane) to generate the desired product as a yellowish oil (117 mg, 0.29 mmol, 84%).

$^1$H NMR (500 MHz, CDCl$_3$) δ 6.76 (d, J=8.2 Hz, 1H), 6.19 (d, J=8.2 Hz, 1H), 4.19 (d, J=2.3 Hz, 2H), 4.11 (td, J=4.8, 2.6 Hz, 2H), 3.94-3.89 (m, 2H), 3.83 (t, J=5.0 Hz, 2H), 3.80 (dd, J=9.0, 3.1 Hz, 1H), 3.74 (dd, J=5.8, 3.6 Hz, 2H), 3.71-3.65 (m, 7H), 3.30-3.23 (m, 1H), 3.20-3.14 (m, 1H), 2.95 (br, 1H), 2.90-2.82 (m, 2H), 2.42 (t, J=2.3 Hz, 1H), 1.93-1.79 (m, 2H), 1.76-1.50 (m, 4H). $^{13}$C NMR (126 MHz, CDCl$_3$) δ 154.4, 153.9, 128.6, 122.1, 114.7, 102.7, 79.5, 74.5, 73.4, 70.8, 70.6, 70.4, 69.7, 69.0, 67.4, 58.3, 53.9, 52.4, 49.9, 43.8, 34.4, 33.3, 24.5. HRMS (ESI-TOF) Calcd. for $C_{23}H_{32}N_2O_4$ [M+H]$^+$: 401.2435; found: 401.2440.

Example 3

Procedure for Chiral Resolution of Compounds 36 and 37

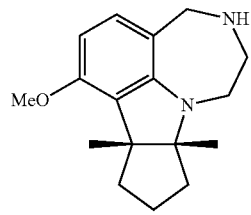 [SMILES: COc1ccc2c3c1[C@@]1(C)CCC[C@@]1(C)N3CCNC2]

Enantiomer A, (R, R) Compound 36

The racemic mixture (507.6 mg, 2.08 mmol) was dissolved in isopropanol (19.6 mL) at room temperature and di-p-toluoyl-L-tartaric acid (401.4 mg, 1.04 mmol) was added all at one time to yield a yellowish solution. The mixture was stirred at room temperature for 15 hours then warmed to 84° C. and stirred for 3 hours. The mixture was cooled to room temperature slowly. The solids were filtered and washed with isopropanol (20 mL) and air dried to yield diastereomeric salts with 2:1 ratio of WAY163909:di-p-toluoyl-L-tartaric acid as a light yellowish powder (273 mg, 0.31 mmol, 30% yield). The diastereomeric salt was partitioned between ammonium hydroxide and dichloromethane and the organic layers were combined, dried over Na$_2$SO$_4$ and evaporated to give the enantiomer A (>95% ee).

Enantiomer B, (S, S), Compound 37

The racemic mixture (505.6 mg, 2.07 mmol) was dissolved in isopropanol (20 mL) at room temperature and di-p-toluoyl-D-tartaric acid (400 mg, 1.04 mmol) was added all at one time. The mixture was stirred at room temperature for 10 minutes, upon which precipitation formed. The mixture was then warmed to 82° C. and stirred for 2 hours. The mixture was then cooled to room temperature slowly. The solids were collected on a Buchner funnel and washed with isopropanol (20 mL) and air dried to yield a diastereomeric salt with 2:1 ratio of WAY163909:di-p-toluoyl-D-tartaric acid as a slight yellowish colored powder (320 mg, 0.37 mmol, 35% yield). The diastereomeric salt was partitioned between ammonium hydroxide and dichloromethane and the organic layers were combined, dried over Na$_2$SO$_4$ and evaporated to give the enantiomer A (>95% ee).

Determination of Enantiomeric Excess (ee)

The resolved diastereomeric salt was partitioned between ammonium hydroxide and dichloromethane. The ammonium hydroxide layer was extracted two more times with dichloromethane. The combined organic layers were dried over Na$_2$SO$_4$ and evaporated to dryness. The enantiomeric purity was determined by adding same weight of (R)-(−)-1,1'-binaphthyl-2,2'-diyl hydrogen phosphate to the free-based material and proton NMR was performed. CDCl$_3$ was used as NMR solvent and calibrated to 7.26 ppm as internal standard. The enantiomer A possesses two doublets at 6.78-6.8 ppm and 6.26-6.27 ppm. The enantiomer B possesses two doublets at 6.58-6.6 ppm and 6.02-6.04 ppm.

Example 4

Compounds were submitted to CEREP to determine receptor selectivity at the 5-HT2 Compounds were tested at a single concentration of 10 μM in duplicate to determine their ability to displace [$^{125}$I]-(±)-DOI. The data are presented as mean percent inhibition of control specific binding for compound tested at each receptor subtype (Table 2). Significant inhibition is considered >50%; 25-50% inhibition is indicative of weak to moderate effects.

We claim:

1. A compound of Formula I or a pharmaceutically acceptable salt thereof, wherein:

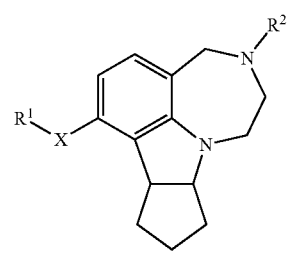

Formula I

R$^1$ is selected from the group consisting of alkyl, polyether tether, and fluorophore;
R$^2$ is a N-protecting group or hydrogen; and
wherein X is O or S;
wherein R$^1$ is a polyether tether with the following structure:

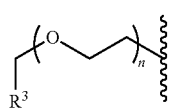

wherein R$^3$ is an alkynyl, fluorophore, or —CH$_2$—R$^4$, wherein R$^4$ is azido, —CO$_2$H, or —NH$_2$;

TABLE 2

Selectivity Profile of WAY163909 Derivatives at 5-HT$_2$R

| Cpd # | Structure | 5-HT$_{2A}$R | 5-HT$_{2B}$R | 5-HT$_{2C}$R |
|---|---|---|---|---|
| 36 | 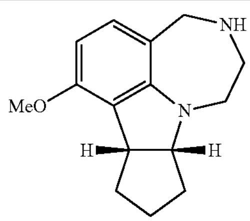 [SMILES: COc1ccc2c3c1[C@H]1CCC[C@H]1N3CCNC2] | 86.5 | 98.6 | 100.2 |
| 37 | 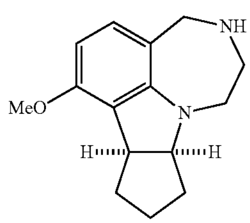 [SMILES: COc1ccc2c3c1[C@@H]1CCC[C@@H]1N3CCNC2] | 22.8 | 4.8 | 91.5 |
| 45 | | 67.1 | 67.7 | 99.6 | and wherein n=1, 2, 3, 4, 5, 6, 7, or 8; and wherein said fluorophore is selected from the group consisting of:
Alkyne cyanine dye 718,
Alkyne MegaStokes dye 608,
Alkyne MegaStokes dye 673,
Alkyne MegaStokes dye 735,
Azide cyanine dye 728,
Azide-fluor 488,
Azide-fluor 545,
Azide-PEG3-biotin conjugate,
Biotin-PEG4-alkyne,
Cy3-alkyne,
Cy3-azide,
Cy5-azide,
DBCO-Cy3,
DBCO-Cy5,
Dibenzocyclooctyne-fluor 488,
Fluor 488-Alkyne,
Fluor 545-Alkyne, and
NVOC2-Q-rhodamine-5-PEG3-azide.

2. The compound of claim 1, wherein X is O; R² is hydrogen.

3. The compound of claim 1, wherein R² is hydrogen; and X is O:

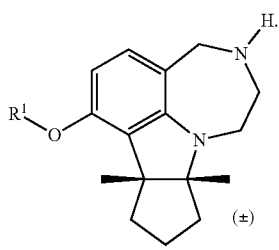

Formula II

4. The compound of claim 1, wherein R² is a N-protecting group selected from the group consisting of CBz and —(CO)R⁵, wherein R⁵ is alkyl or aryl.

5. The compound of claim 2, wherein the compound is one of:

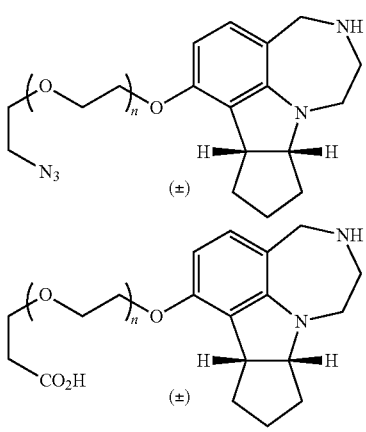

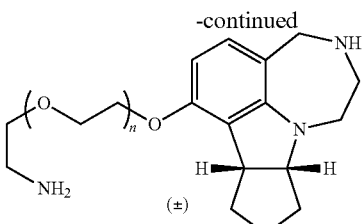

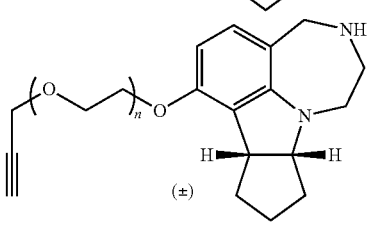

wherein n=1, 2, 3, 4, 5, 6, 7, or 8.

6. The compound of claim 1, wherein; R² is a N-protecting group; and X is O:

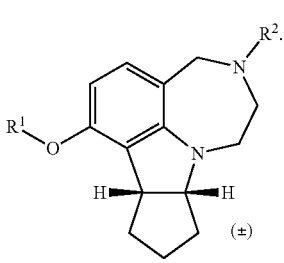

Formula III

7. The compound of claim 1, wherein R² is a N-protecting group or hydrogen; and X is O:

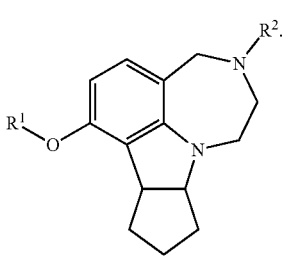

Formula Ia

8. The compound of claim 3, wherein R¹ is methyl:

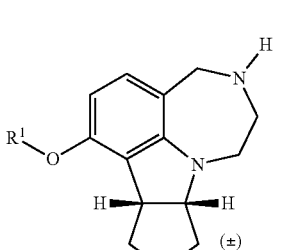

* * * * *